United States Patent [19]

Yamamoto et al.

[11] Patent Number: 4,676,782

[45] Date of Patent: Jun. 30, 1987

[54] POSITIONABLE TISSUE INTERFACING DEVICE FOR THE MANAGEMENT OF PERCUTANEOUS CONDUITS

[75] Inventors: Ronald K. Yamamoto, Redwood City; Sophia Pesotchinsky, San Jose, both of Calif.

[73] Assignee: Vitaphore Corporation, San Carlos, Calif.

[21] Appl. No.: 862,766

[22] Filed: May 13, 1986

Related U.S. Application Data

[63] Continuation-in-part of Ser. No. 653,442, Sep. 21, 1984, abandoned.

[51] Int. Cl.$^4$ .............................................. A61M 5/00
[52] U.S. Cl. ...................................... 604/175; 604/265
[58] Field of Search .................. 604/53, 106, 27, 29, 604/165, 174, 175, 265, 280

[56] References Cited

U.S. PATENT DOCUMENTS

| | | | |
|---|---|---|---|
| 2,456,257 | 12/1948 | Curry | 604/106 |
| 3,461,869 | 8/1969 | Hargest . | |
| 3,633,585 | 1/1972 | McDonald . | |
| 3,638,649 | 2/1972 | Ersek . | |
| 3,663,965 | 5/1972 | Lee et al. | 3/1 |
| 3,699,956 | 10/1972 | Kitrilakis et al. . | |
| 3,769,975 | 11/1973 | Nimoy et al. | 604/165 |
| 3,856,021 | 12/1974 | McIntosh | 604/175 |
| 4,054,139 | 10/1979 | Crossley . | |
| 4,217,664 | 8/1980 | Faso | 3/1 |
| 4,266,999 | 5/1981 | Baier | 156/227 |
| 4,278,092 | 7/1981 | Borsanyi et al. . | |
| 4,392,855 | 7/1983 | Oreopoulos et al. | 604/175 |
| 4,405,313 | 9/1983 | Sisley et al. | 604/280 |
| 4,412,832 | 11/1983 | Kling et al. | 604/280 |
| 4,479,795 | 10/1984 | Mustacich et al. | 604/265 |
| 4,484,911 | 11/1984 | Berlin et al. | 604/174 |
| 4,491,126 | 1/1985 | Cullor | 604/175 |
| 4,515,593 | 5/1985 | Norton | 604/265 |

OTHER PUBLICATIONS von Recum, A. and Park, J. B., "Permanent Percutaneous Devices", CRC Critical Reviews in Bioengineering, 5:37-77 (1981).

Primary Examiner—C. Fred Rosenbaum
Assistant Examiner—Sherri Vinyard
Attorney, Agent, or Firm—Christie, Parker & Hale

[57] ABSTRACT

This invention is a sleeve-like tissue-interface device designed to reduce the incidence of nosocomial infection related to percutaneous conduits by promoting a tissue seal where the conduit and skin interface, and by the expression of antibacterial activity to reduce the possibility of bacteria advancing along the conduit into deeper tissues. In particular, the positionability of the invention allows it to be placed onto a catheter-like device, in the dermal and subcutaneous tissue below the catheter exit site, although this position relative to catheter length is variable at different anatomical sites, and from patient to patient. The positionability feature also allows the invention to be used in conjunction with existing percutaneous access devices such as catheters and wound drains, as an optional measure against bacterial infection.

21 Claims, 23 Drawing Figures

POSITIONABLE TISSUE INTERFACING DEVICE FOR THE MANAGEMENT OF PERCUTANEOUS CONDUITS

This application is a continuation-in-part of U.S. patent application Ser. No. 653,442 filed on Sept. 21, 1984, now abandoned.

FIELD OF THE INVENTION

This invention relates to a device for the improved management of microbial invasion associated with percutaneous conduits, and more particularly to a design which allows the device to be used in conjunction with an existing conduit and positioned along the length of the conduit to a desire anatomical site for optimal effectiveness.

DESCRIPTION OF THE PRIOR ART

A percutaneous device or conduit is an implement which passes through the skin, allowing the linkage of an intracorporeal organ or cavity with extracorporeal equipment. There exists a wide variety of clinical applications for percutaneous devices. In the facilitation of fluid transport, percutaneous conduits called catheters are used to access blood for dialysis, pressure monitoring, or laboratory diagnosis, to deliver drugs or nutritional solutions, and to drain wound exudate. Percutaneous electrical leads are used to allow the monitoring of biopotentials from natural organs or implanted instrumentation, as well as for stimulation of such organs. Percutaneous orthopedic fixation pins are used to immobilize severely damaged bone by mechanical coupling to a rigid external frame.

Despite the widespread clinical need and usage of percutaneous conduits, the presence of the conduit eventually results in bacetrial infection, compromising the health of the patient and forcing conduit removal.

Figure 1:
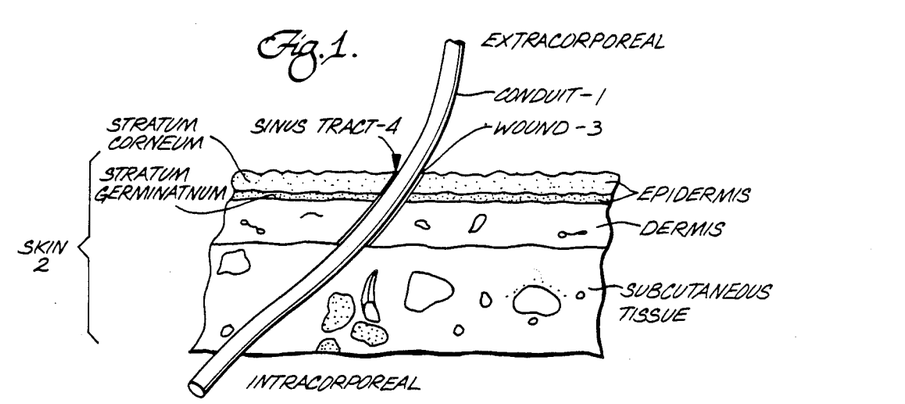
FIG. 1 shows the anatomical relationship between a percutaneous conduit, the skin and the body surface.

FIG. 1 depicts the anatomical relationships referred to in the followinig description of the infection mechanism associated with percutaneous conduits. a conduit 1 spans the various layers of the skin 2. The portion of the conduit which lies outside the body is referred to as extracorporeal, while that within the body is intracorporeal. Conduit 1 is implanted through a wound 3 in the skin, the wound having been made either expressly for the purpose of inserting the conduit or as a result of an injury. In either case, a sinus tract 4 is formed by ingrowth of epithelium into the wound. A good review of the biology and failure mechanisms associated with percutaneous devices can be found in *CRC Critical Reviews in Bioengineering*, Vol. 5, pp. 37-77, 1981, by A. F. von Recum and J. B. Park.

Bacteria that have penetrated beneath the epithelium-conduit interface into underlying tissues find a favorable environment for colonization. The tissues contacting implanted foreign bodies are in a state of chronic inflammation, impairing the normal defense mechanisms against bacterial infection, a basis for the commonly accepted fact that wounds containing foreign bodies are more susceptible to infection (Willliams and Road, *Implants in Surgery*, 241-244, W. B. Saunders Co., Ltd. 1973). A classic study demonstrated that while $7.5 \times 10^6$ viable staph aureus organisms were necessary to produce a skin infection, only $3 \times 10^2$ organisms produced an infection in the presence of a silk stitch inserted in the wound (Elek and Conen, *British Journal of Experimental Pathology*, 38:573, 1957). A more recent study has indicated the phagocytosis of bacteria by leukocytes, the secondary defense against bacterial invasion, is impaired in the presence of some foreign materials, at least in vitro (Borges, L. F., *Neurosurgery*, 10:55-60, 1982). Once established, bacterial infections around implanted foreign materials usually cannot be managed even with massive antibiotic therapy, forcing removal of the implant.

The advance of bacterial colonization along the conduit surface and interfacing tissues may also result in peritonitis when the peritoneal cavity is penetrated by the conduit. Similarly, joint capsule infection may occur when a wound is drained after orthopedic surgery, and septicemia may result when the vascular system is accessed by an intravenous or arterial line. The constant bacterial challenge and threat of infection created by percutaneous conduits forces conduit removal and replacement in alternate areas when possible, and either discontinuation of the function of the conduit or increased risk of infection when not possible.

The bacterial organisims which initiate infections associated with percutaneous conduits are part of the normal flora on the skin, ranging in density from 10 to $10^6$ organisms per square centimeter. Normally these organisms are unable to colonize into deeper tissues and proliferate, as they cannot penetrate the primary barrier against infection, the epidermal layer of the skin. The presence of a percutaneous conduit requires disruption of this barrier, through which bacteria can invade deeper tissues.

The perimeter at the conduit interface does not seal, even after sufficient time for wound healing. The new healing epithelium, upon reaching the conduit, does not recognize and adhere to the foreign body, but instead grows down along the conduit in an effort to externalize the foreign body, forming a sinus tract 4 which is a pathway for bacterial invasion. A recent clinical study has indicated significant association of bacterial colonization of percutaneous catheters and the density of bacteria present on the skin at the exit site, as one would expect from the infection pathway (Bjornson, et al., Surgery, Vol. 92, No. 4, pp. 720-726, 1982).

The lack of a seal of the conduit to the dermal and epidermal tissues not only allows access for bacteria, but also prevents mechanical loads from being transferred between the tissues and the conduit. The mechanical discontinuity causes a crevice between the tissues and the conduit to open and close when the conduit is mechanically stressed, or when the tissues move during normal muscle usage, thus promoting bacterial invasion.

In order to reduce the ever-present threat of infection associated with ercutaneous conduits, devices to improve the tissue interface at the percutaneous area or zone (dermis- and epidermis-conduit interface) have been constructed. The use of porous material which promotes tissue ingrowth from the tissue layers below the epidermis has shown effectiveness in inhibiting epidermal downgrowth (sinus tract formation) and promoting a seal at the epidermal- and dermal-conduit interface (Lee, U.S. Pat. 3,663,965; Borsanyi, U.S. Pat. No. 4,278,092). However, porous materials with interconnected porosity, such as velours, felts, foams, and sponges, have a disadvantage in that once infected, the material acts as a wick, allowing the bacteria to colonize the pores filled with wound exudate and wound debris in areas not readily accessible to host defense cells.

Other attempts at combating bacterial infection related to percutaneous conduits involve the application of antibacterial agents, either to the conduit surface (Crossley, U.S. Pat. No. 4,054,139), or in a fluid reservoir device constructed around the conduit in the subcutaneous tissue just below the conduit exit site (Kitrilakis, et al., U.S. Pat. No. 3,699,956).

Several problems arise when using a tissue interfacing device at the percutaneous interface to help reduce the incidence of infection. The use of devices which have bulky subcutaneous flanges (Faso, U.S. Pat. No. 4,217,664) or antibacterial fluid reservoirs (Kitrilakis, supra) require surgical manipulation of tissues to properly place the device. If the device has a tissue sealing design using porous material such as a velour sleeve, the material should be located close to the dermis-conduit interface. Misplacement in the intracorporeal direction will allow mechanical discontinuity at the critical dermis-to-conduit interface, and also will not allow the epidermis and dermis to grow into the porous material to provide a bacterial seal. Misplacement in the extracorporeal direction will create passageways for bacteria through the pores and immediately introduce external skin bacteria to colonize the porous material.

Also, when implanting a percutaneous conduit with an attached percutaneous device, or otherwise designated percutaneous area, the length of conduit from the percutaneous exit site to the intracorporeal end is desired to be variable, to allow for the anatomical geometry of the particular patient. Inaccuracies involved in estimating this length may cause the improper location of the percutaneous tissue-interfacing device in the tissue layers of the integument, the improper location of the intracorporeal end, undesirable slack in the conduit, or a need for trial fittings to establish the correct length.

The percutaneous tissue-interfacing device of this invention is easily positionable along the conduit length to provide flexibility for optimal device placement during the surgical procedure. Additionally, the ability to be quickly positioned and attached to a preexisting percutaneous conduit allows the device to be used as an optional measure for patients at high risk for infection.

SUMMARY OF THE INVENTION

The invention comprises a tissue interface device designed to be placed onto a separate percutaneous conduit and positioned along the conduit length to a desired anatomical site for effective infection resistance. The invention can be implemented at the time of conduit implantation, or at a later time at the discretion of the clinical practitioner, due to a design which allows the tissue interface device to be implanted from the extracorporeal side using the wound created for conduit entry.

Briefly, the invention comprises a sleeve with elastic properties which is dilated with the aid of a special introducer and is then placed over a conduit or catheterlike device. The dilated sleeve and introducer may then be moved near the external catheter hub or proximal end, to be out of the way during surgical placement of the distal or intracorporeal portion of the percutaneous conduit. As a final step, the sleeve-introducer combination is moved along the conduit, placing the sleeve into the subcutaneous tissue just beneath the conduit skin exit site. When the introducer is removed, the elastomeric properties of the sleeve material cause its diameter to decrease, resulting in radial compression against the conduit, thus securing the sleeve.

The outer tissue-interfacing surface of the device is designed to reduce the incidence of infection related to percutaneous conduits by two basic mechanisms: (a) promotion of a tissue-to-conduit seal at the skin (epidermis, dermis, and adjacent subcutaneous tissues) to conduit interface, and (b) the use of antibacterial agents incorporated into the device to reduce the possibility of bacteria colonizing the foreign materials (especially during the initial formation of a tissue seal) and advancing along the conduit into deeper tissues. In addition, the use of a tissue ingrowth material provides mechanical fixation of the percutaneous conduit without the use of sutures, thus discouraging accidental conduit displacement.

The inner conduit-interfacing surface of the sleeve is designed primarily for firm frictional contact with the conduit, but can be composed of an elastomer impregnated with an antimicrobial agent to prevent bacterial invasion between the device and conduit. Such an inner sleeve surface also acts as a "bacterial squeegee" to prevent contamination should the extracorporeal side of the conduit slip through the sleeve into the tissues.

DESCRIPTION OF THE PREFERRED EMBODIMENTS

Figure 2:
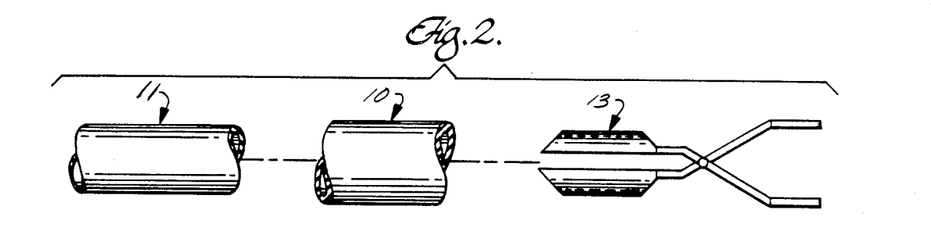
FIG. 2 illustrates the relationship between a conduit, a sleeve and an introducer.

Referring to FIG. 2, a first-embodiment device of the present invention is a resilient sleeve 10 having a relaxed inside diameter smaller than the outside diameter of a conduit such as a catheter 11 on which the sleeve will be mounted. The catheter may be provided with a conventional syringe fitting or similar connection hub 12 (FIG. 3) at its outer or proximal end. The term "conduit" is herein used in a general sense to include hollow tubular catheters as well as other types of elongated body-insertable members (either solid or hollow) such as electrical leads or orthopedic pins.

To enable fitting of sleeve 10 over catheter 11, the sleeve is elastically dilated by an expansion tool or introducer 13 (further described below) which is inserted into the sleeve bore and activated to expand the sleeve diameter. The implantable distal end of the catheter is then inserted through the introducer and expanded sleeve to position the sleeve temporarily toward the catheter proximal end adjacent hub 12. If the catheter is not provided with a hub or similar enlargement at it proximal end, this preliminary step of threading the sleeve on the catheter can be deferred until the distal catheter end has been implanted.

Figure 3A:
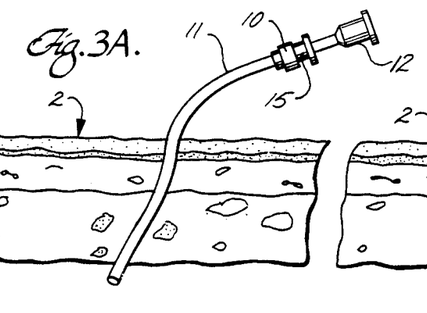
FIG. 3 shows how a sleeve is positioned by an introducer on a conduit.
Figure 3B:
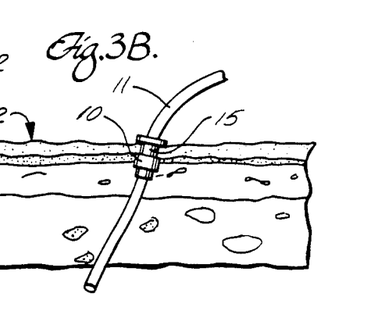

After this preliminary step of positioning the sleeve, the distal end of the catheter is implanted using appropriate conventional surgical tecnhiques, and the various components are then positioned as shown in FIG. 3A which illustrates an alternative introducer 15 described below. When catheter positioning is completed, the introducer is again activated to expand the sleeve so it can be slipped along the catheter into the tissues just beneath the skin surface as shown in FIG. 3B. Activating finger pressure on the introducer is then released, enabling the introducer to be withdrawn from the sleeve by a slight side-to-side rocking or lateral wiggling motion combined with a rearward extracting force moving the introducer proximally out of the bore of the implanted sleeve.

Figure 4A:
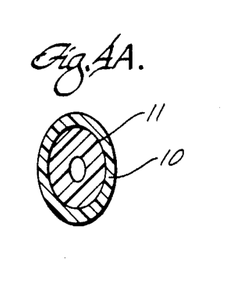
FIG. 4 shows differently shaped conduits in cross section.
Figure 4B:
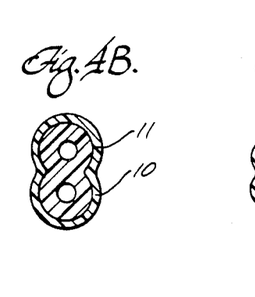
Figure 4C:
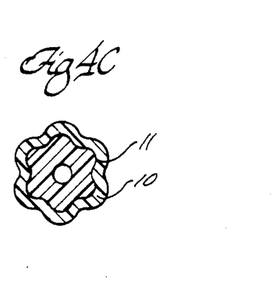

Essential to the positionability of the device is the elastic property of the sleeve material. This allows high material strain, corresponding to large device dilation, and use of the stored strain energy to provide a radial clamping force upon release. The high deformability of the elastomeric material also provides clamping and sealing of sleeve 10 to the catheter of similar conduit, even if the conduit cross-section is ellipsoid (FIG. 4A) or has a complex geometry (FIGS. 4B and 4C). Any elastomer with negligible stress-relaxation properties and a high elastic limit is suitable mechanically. It is also desirable from a physiological viewpoint that the elastic material have minimal inflammatory effect on the surrounding tissue. Several types of medical grade elastomers, such as polydimethyl siloxanes (silicone rubbers) or related polymers, polyurethanes and polyisoprenes are suitable.

Essential to the infection reduction properties of the invention is the outer tissue-interfacing surface of sleeve 10. The surface is desired to express both antibacterial activity and tissue sealing properties.

The antibacterial properties can be conferred by (1) bulk incorporation of antibacterial agent into the sleeve material, (2) surface coating of antibacterial agent, or (3) attachment of a tissue ingrowth promoting material with incorporated antibacterial activity. In some applications, it is desirable to provide these antibacterial properties within the sleeve bore as well as on the outer surface. The tissue sealing properties can be conferred by (a) the attachment of porous, tissue ingrowth promoting material, such as woven felts, and velours, textured polymers, and foam or spong-like materials, (2) the surface texturing of the sleeve material by high energy bombardment or salting out methods; (3) the attachment or incorporation of tissue adhesive biomolecules such as lectins.

Generally, the tissue-interfacing sleeve of this invention will have antibacterial surface properties conferred by one of the methods previously described. It is also preferrd to have tissue adhesive properties without the use of relatively permanent porous tissue ingrowth materials. The use of adhesive biomolecules on the outer surface, or biodegradable tissue ingrowth materials such as collagen sponge, or a combination of the two, is preferred, as ease of device removal will not become compromised.

Figure 5:
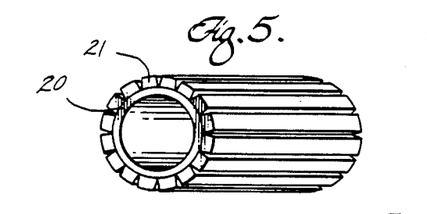
FIG. 5 shows a conduit with longitudinally placed tissue ingrowth material.

In a second embodiment of the present invention, shown in FIG. 5, a resilient sleeve 20 will have an irregularly surfaced porous tissue ingrowth material 21, attached on the outer sleeve surface in longitudinal strips for sufficient radial dilation. The ingrowth of subcutaneous and dermal tissue into the pores will form a seal around the conduit, reducing the sinus tract pathway for bacterial invasion around the catheter. As ingrowth materials with interconnecting porosity (i.e., velours, felts, foams, sponges) can conduct bacterial infection once established, such materials will incorporate an antibacterial agent to prevent bacterial "wicking." Additionally, it is desirable to use biodegradable materials for the ingrowth layer, so that when catheter removal is indicated, the ingrowth material can be left in situ for resorption, thereby alleviating the need for surgical excision. Some potential resorbable materials are sponges or foams prepared from collagen, polypeptide, polyactic acid, and polyamino acids. Surface texturing can be used in combination with incorporation of antibacterial activity into or onto the sleeve material as previously described.

The thickness, inside diameter and outside diameter of the sleeve will depend on the outside diameter of the conduit and its radial compliance, the properties of the sleeve material, and the coefficient of friction between the conduit outer surface and the sleeve inner surface. The dimensions of a compliant sleeve material are less critical than in a material which is less compliant. Similarly, the greater the coefficient of friction of either the conduit or sleeve, the less the sleeve will tend to slide longitudinally on the conduit, leading to a correspondingly reduced need for radial compression of the conduit by the sleeve to fix the latter in place. The thickness of an attached porous ingrowth layer will depend on the outside diameter of the sleeve, the expected loads on the percutaneous interface, the degradation rate of the ingrowth layer if it is biodegradable, and the intended period of clinical use.

Yet another and presently preferred embodiment of the invention is shown in FIGS. 6A–D which illustrate a sleeve assembly 25 having a corelike resilient sleeve 26 (preferably molded from a medical-grade silicone elastomer) of somewhat "dogbone" or "barbell" shape. The opposed ends of the sleeve are reduced in diameter to form outwardly tapered leading and trailing (distal and proximal) end surfaces 27 and 28. As in the other embodiments already described, the sleeve has a central bore 29 extending therethrough, and the bore has a relaxed inside diameter somewhat smaller than the outside diameter of a catheter 30 (FIG. 60) or a similar implantable conduit on which the sleeve assembly will be installed.

Sleeve 26 is reduced in diameter between tapered end surfaces 27 and 28 to define an annular recess 32 into which is fitted a cylindrical ring-like porous sponge 33 (made of any of the materials described above, but preferably of cross-linked collagen) impregnated with an antimicrobial agent. The inner surface of the sponge is secured to the outer surface of sleeve 26 in recess 32 by a thin layer of adhesive 34 (a conventional medical-grade silicone-elastomer adhesive is suitable).

The sponge is dilated to fit over one of the enlarged ends of sleeve 26 into recess 32, and then permitted to resiliently contract against the sleeve and adhesive. To simplify this installation process, the sponge can be formed in two short sections 33a and 33b which abut each other at their inner ends, and which fit snugly between the end walls of the sleeve recess. Alternatively, the sponge (formed either as a unit or as multiple elements) can be held in a sleeve mold (not shown) so the sleeve can be molded in situ within the sponge.

Figure 6A:
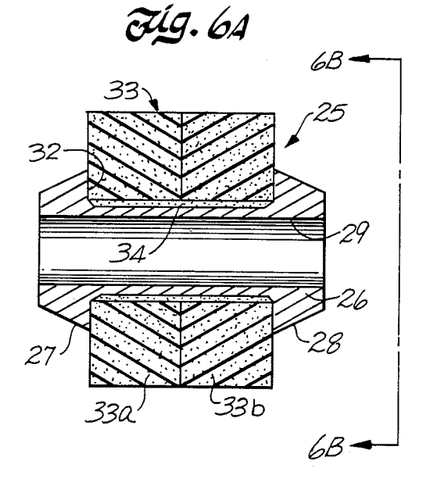
FIG. 6 shows a presently preferred embodiment of a sleeve according to the invention.
Figure 6B:
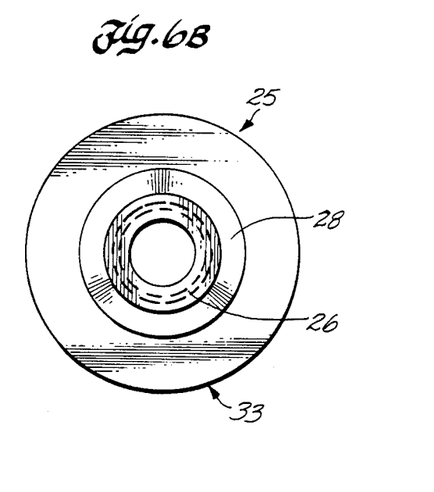
Figure 6C:
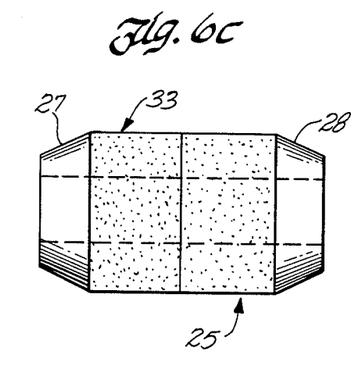

After initial installation as shown in FIGS. 6A-B, the sponge is compressed in a die to be reduced in outside diameter (as shown in FIG. 6C) so the sponge is confined within recess 32, and the sleeve assembly has a smooth cylindrical appearance of constant outside diameter between the tapered end surfaces. The sponge material maintains a "set" in the compressed position until exposed to tissue fluids as described below, thereby easing insertion of the sleeve assembly into the tissue.

Assembly 25 is fitted over the catheter using a dilating introducer as already described, and this step is completed prior to catheter implantation if the catheter has a hub at its proximal end, or can be delayed until after implantation for a hubless catheter. In either event, the sleeve is again dilated with the introducer after the catheter is implanted, and the expanded sleeve is slipped along the catheter to a position just beneath the skin. The introducer is then removed as described above to leave the sleeve in tight, resiliently clamped engagement around the catheter.

Tapered end surfaces 27 and 28 assist in both implantation of the sleeve, and in healing of the catheter entrance incision. The leading taper allows easy mechanical entry of the device into a very small incision to insure a snug fit and good bacterial seal. The trailing taper allows the natural skin elasticity to close the incision after the sleeve is placed in subcutaneous tissue, helping to prevent dislodgement of the sleeve and catheter during incision healing. The aforementioned compression of sponge 33 into the sleeve recess similarly assists in implantation of the sleeve assembly in a small incision, and minimizes risk of sponge damage during this installation step.

Figure 6D:
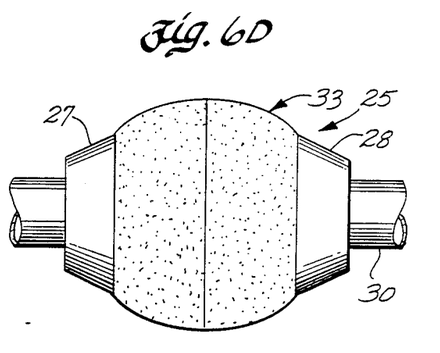

Within minutes after subcutaneous placement of the sleeve assembly, sponge 33 absorbs water from the surrounding tissue, and swells as shown in FIG. 6D to provide nearly immediate mechanical stabilization prior to tissue ingrowth, thus insuring a snug fit within the tissue as is essential for an early bacterial seal. The sponge will typically double in volume as fluid is absorbed, providing the desired significant radial expansion, tight tissue contact, and favorable ingrowth surface. Most of the expansion desirably occurs in the central part of the sponge due to frictional contact of the spong end surfaces with the sidewalls of recess 32.

In a typical configuration suitable for fitting over a 16-gauge medical catheter or comparable conduit, sleeve 26 has an inside diameter of about 0.055 inch, an outside diameter in recess 32 of about 0.076 inch, an overall axial length of about 0.234 inch, and a recess axial length of about 0.150 inch. The leading and trailing end surfaces are tapered at about 25 degrees to diminish from a maximum outside diameter of about 0.130 inch to a minimum outside diameter at the sleeve ends of about 0.093 inch.

When the catheter or similar conduit is to be removed from the patient after long-term implantation, a sharp pull on the external catheter will separate sleeve 26 from sponge 33 so the sleeve is removed with the catheter. The tissue-bound outer portion of the sponge is left in the body where it is absorbed.

Clamping force of the resilient sleeve on the catheter is primarily determined by the size of the sleeve bore which is somewhat smaller than the catheter outside diameter, but is also somewhat dependent on the frictional characteristics, wall thickness, radial compliance, and durometer of the materials used, and the relative sizes of the sleeve and catheter which establish the surface areas which are in frictional contact. Typically, the relaxed inside diameter of the sleeve is selected to be in the range of 80-95 percent of the catheter outside diameter, with smaller sleeves being toward the low end of this range to offset the diminished area of surface contact between the sleeve and catheter. The clamping force should be sufficient to require about one pound of axial (shear) force before relative movement between the sleeve and catheter is permitted.

In certain applications of the sleeve of this invention, it may be desirable to dimension the sleeve bore to be closer to a slip fit over the conduit. For example, orthopedic pins used in bone-fracture cases sometimes extend from the bone percutaneously to an external supporting fixture. In such cases, it is desirable to provide a low-force slipping engagement between the pin and tissue-embedded sleeve to permit relative movement of the pin and sleeve. Similar requirements may arise with percutaneous conduits such as electrical leads or diagnostic catheters.

In these limited-motion applications, the sleeve bore is only slightly smaller than the conduit diameter, and preferably the sleeve bore is provided with an antimicrobial substance to prevent bacterial invasion from the skin inwardly along the sleeve-conduit junction. The sleeve then acts as a bacterial "squeegee" which wipes and inactivates bacteria on the conduit surface during conduit-sleeve movement, thereby maintaining a bacterial seal at the skin interface.

With further reference to the introducers briefly mentioned above, these tools are used to dilate the sleeve to allow its positioning over the conduit. The following examples are given for illustrative purposes.

FIGS. 7A-D and 8 show a cylindrical introducer 15 with a tapered end 40, a flange 41 on the other end, and perforation lines 42 (or equivalent lines of weakness) along the length of the introducer and radially opposed to each other. The perforation lines enable the introducer to be split into two sections either before installation in the sleeve, or during removal from the sleeve.

Figure 7A:
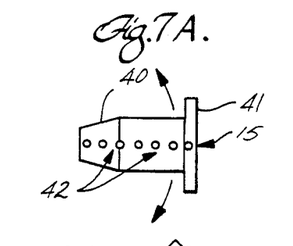
FIG. 7 shows one type of introducer.
Figure 7B:
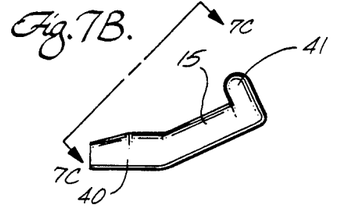
Figure 7C:
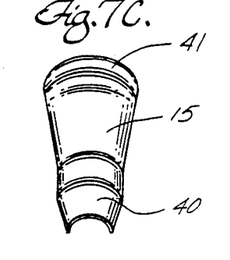
Figure 7D:
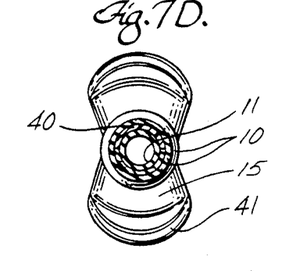
Figure 8:
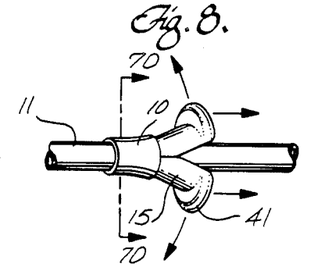
FIG. 8 illustrates the use of an introducer of the type shown in FIG. 7.

Introducer 15 is preferably manufactured in two separate pieces, one of which is shown in end and edge views in FIGS. 7B and 7C respectively. In using this introducer, the two halves are placed together as shown in FIG. 7D. Tapered end 40 of the introducer is then pushed into a sleeve 10 (configured according to the invention), dilating it, and the assembly of introducer and sleeve is pushed onto the conduit as shown in FIG. 8. When the sleeve is correctly positioned, the two halves of the introducer are pulled apart to slip from within the sleeve.

An advantage of the two-piece design is that the introducer may be easily removed from the site of conduit implantation without threading the length of the conduit through the introducer. The introducer may be formed of a plastic material or of metal, but is preferred that the material be slightly flexible. An advantage of using a plastic material is that the introducer may be both sterile and disposable.

Figure 9A:
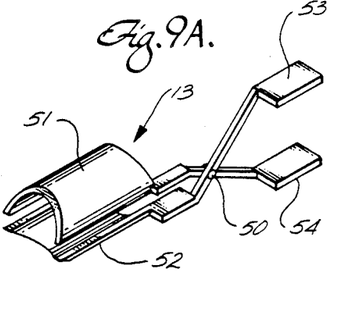
FIG. 9 illustrates an alternative embodiment of an introducer.
Figure 9B:
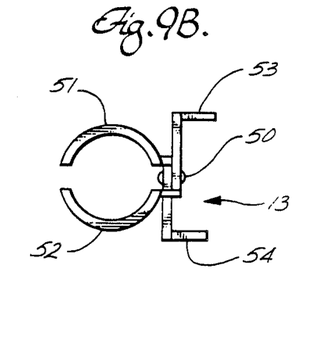

An alternate embodiment of a "scissor" introducer 13 as shown in FIGS. 9A and 9B, and using two arm-like components joined at a pivot 50, allows the sleeve to be placed over split cylinder sections 51 and 52, and dilated when pressure is applied to actuation pads 53 and 54. The introducer and sleeve are placed over the catheter or conduit, and brought to the desired location. The pressure on the actuation pads is released as the introducer is pulled away from the sleeve, leaving the sleeve on the conduit.

Any rigid polymer which is readily sterilizable and moldable is suitable for the construction of the introducers. Some examples are polyethylene, polypropylene, and polysulfone. An introducer design such as just described is not permanently deformed during use, and can be reused. A variety of metals and rigid polymers are suitable for its construction.

Alternative sleeve-like designs utilizing elastic components to provide residual clamping force for fixation are possible, combined with the tissue sealing components and the incorporation of antibacterial activity as previously described.

Figure 10:
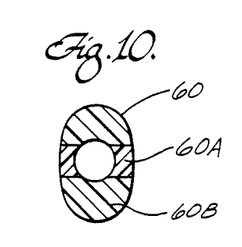
FIG. 10 shows an alternative embodiment of the sleeve of FIG. 2.

FIG. 10 shows a composite device design utilizing elastomeric components 60 to provide positionability of the device, and is a simple modification although device complexity is increased. Such a sleeve may be formed in two parts comprising an elastomeric region 60A and a nondistensible region 60B bonded to elastomeric region 60A.

Figure 11A:
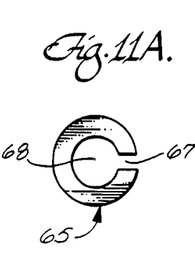
FIG. 11 shows another alternative embodiment of a sleeve.
Figure 11B:
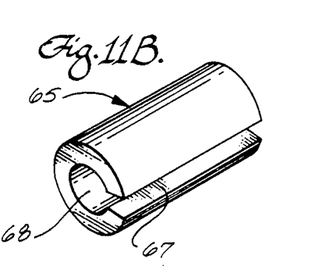

A discontinuous sleeve 65 with, for example, a C-shaped cross-section when deformed is shown in FIGS. 11A-B. This sleeve can be placed without high dilation by pressing a conduit through a slit-like opening 67 into a central lumen 68. Release of the device will allow elastic return to apply a clamping force, although not as efficiently as an integral, cylindrical sleeve. This embodiment of the invention can also be used with the introducers already described.

Figure 12:
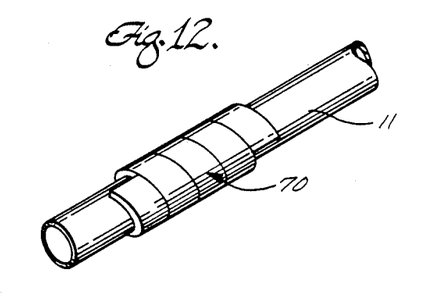
FIG. 12 shows yet another embodiment of a sleeve, where the sleeve is wound around the conduit.

A coiled sleeve 70 shown in FIG. 12 consists of a strip of resilient material wound into a helical sleeve which can be deformed and placed around a catheter-like tube without high material deformation, yet utilizing the deformation to provide a residual clamping force, although the magnitude of the force will not be as great as in the previously described embodiments. An advantage of coiled sleeve 70 is that an introducer is not required.

Finally, it should be emphasized that these designs may also be used to secure conduits in deep tissue sites, as, for example, when electrical leads need to be implanted in regions of high mobility such as joints, blood vessels, the heart, or in the bowel.

What is claimed is:

1. An implantable device for providing a circumferential bacterial seal and sutureless tissue fixation to a percutaneous conduit of known outside diameter, comprising a distensible elastomeric sleeve having a relaxed inside diameter smaller than said known diameter, and having sufficient resiliency to enable forcible expansion of the inside diameter so the sleeve can be moved along the conduit into an implanted intracorporeal position beneath a skin exit site at any desired longitudinal position along the conduit, the resiliency of the sleeve providing a restoring force sufficient to place the sleeve in frictional gripping contact with the conduit at said position when the expanding force is removed, the sleeve being formed of a tissue-compatible material and having an outer surface which promotes tissue ingrowth.

2. The device of claim 1 wherein the surface of the sleeve has been impregnated with a substance having antibacterial properties.

3. The device of claim 1 wherein only a portion of the circumference of the sleeve is distensible.

4. The device of claim 1 wherein the circumference of the sleeve is incomplete.

5. the device of claim 1 wherein the sleeve is formed as a helical coil to be wound around the conduit.

6. The device of claim 1 wherein the tissue-ingrowth-promoting surface of the sleeve is provided by a material secured to the sleeve outer surface.

7. The device of claim 1 wherein the tissue-ingrowth material is impregnated with a substance having antibacterial properties.

8. The device of claim 7 wherein the material attached to the outer surface of the sleeve is selected from the group consisting of velour, felt, foam, sponge, collagen, polylactic acid, polyamino acid, and polypeptide.

9. The device of claim 1 wherein the inner surface of the sleeve contacting the percutaneous conduit contains an antimicrobial agent, combined with a sleeve clamping force that allows limited motion of the percutaneous conduit, thereby inactivating bacteria on the outer surface of the perctaneous conduit as it passes through the sleeve to provide an aseptic sliding seal.

10. A method for establishing a percutaneous tissue interface on a percutaneously inserted conduit comprising the steps of:
 dilating a distensible elastomeric sleeve;
 slipping the elastomeric sleeve over the conduit;
 moving the sleeve to a subcutaneous position on the conduit with respect to the conduit intracorporeal and extracorporeal ends; and
 allowing the sleeve to return toward its nondistended diameter to be frictionally clamped to the conduit beneath the skin exit site of the conduit.

11. A method according to claim 10 wherein the sleeve is positioned so as to lie beneath the dermis of the skin but superficial with respect to the subcutaneous fat.

12. The combination comprising a percutaneously inserted conduit having an intracorporeal portion extending beneath a skin exit site, and an elastomeric sleeve in resiliently gripping engagement around the intracorporeal portion of the conduit and resisting longitudinal movement along the conduit, the sleeve being sufficiently elastic to enable forced dilation so the sleeve can be enlarged in inside diameter and slipped along the conduit to a desired subcutaneous position after conduit implantation, the sleeve having an outer surface which promotes tissue ingrowth.

13. The device of claim 12 wherein the tissue ingrowth material is a dry, compressed water-absorbing sponge, such that absorption of fluids after implantation swells the diameter of the sponge to provide rapid mechanical fixation and bacterial sealing of the skin incision.

14. The device of claim 13 wherein the tissue ingrowth material is comprised of cross-linked collagen sponge.

15. The device of claim 13 wherein the tissue ingrowth material contains an antimicrobial agent.

16. An implantable device for fixation of an implanted percutaneous conduit such as a catheter and having a known outside diameter, the device comprising:
 a distensible elastomeric sleeve having tapered ends and an annular recess between the ends, the sleeve having a relaxed inside diameter smaller than the conduit outside diameter, and having sufficient resiliency to enable forcible sleeve dilation so the sleeve can be moved along the conduit to an implanted intracorporeal position beneath a skin exit site of the conduit, the resiliency of the sleeve providing a restoring force sufficient to place the sleeve in frictional gripping contact with the conduit when the expanding force is removed, and a tissue ingrowth material positioned around the sleeve in the recess.

17. The device defined in claim 16 wherein the tissue ingrowth material is a dry, compressed water-absorbing sponge, such that absorption of fluids after implantation swells the diameter of the sponge to provide rapid mechanical fixation and bacterial sealing of the skin incision.

18. The device defined in claim 16 wherein the tissue ingrowth material is a sponge.

19. The device defined in claim 18 wherein the sponge is made of collagen which incorporates an antimicrobial material.

20. The device defined in claims 19 wherein said frictional gripping contact is sufficient to prevent relative movement of the device and conduit responsive to axial forces up to about one pound.

21. The device defined in claim 19 wherein an inner surface of the sleeve which contacts the conduit incorporates an antimicrobial material.

* * * * *